US 8,894,704 B2

(12) United States Patent
Groothuis et al.

(10) Patent No.: US 8,894,704 B2
(45) Date of Patent: Nov. 25, 2014

(54) SYSTEMS AND METHODS FOR TREATING LUMENAL VALVES

(71) Applicants: Adam Groothuis, Swampscott, MA (US); Adrian Ebner, Asuncion (PY); Peter Markham, Kingston, NH (US); Elazer Edelman, Brookline, MA (US)

(72) Inventors: Adam Groothuis, Swampscott, MA (US); Adrian Ebner, Asuncion (PY); Peter Markham, Kingston, NH (US); Elazer Edelman, Brookline, MA (US)

( * ) Notice: Subject to any disclaimer, the term of this patent is extended or adjusted under 35 U.S.C. 154(b) by 0 days.

(21) Appl. No.: 13/868,226

(22) Filed: Apr. 23, 2013

(65) Prior Publication Data

US 2013/0310924 A1    Nov. 21, 2013

Related U.S. Application Data

(62) Division of application No. 12/899,231, filed on Oct. 6, 2010.

(60) Provisional application No. 61/249,020, filed on Oct. 6, 2009.

(51) Int. Cl.
*A61F 2/24* (2006.01)

(52) U.S. Cl.
CPC .............. *A61F 2/2436* (2013.01); *A61F 2/2412* (2013.01); *A61F 2/2427* (2013.01); *A61F 2/2475* (2013.01)
USPC ........................................................ 623/2.11

(58) Field of Classification Search
USPC ........................................ 623/1.12, 2.1, 2.11
See application file for complete search history.

(56) References Cited

U.S. PATENT DOCUMENTS

| 6,419,696 | B1 | 7/2002 | Ortiz et al. |
| 6,869,444 | B2 | 3/2005 | Gabbay |
| 6,974,476 | B2 | 12/2005 | McGuckin et al. |
| 8,292,938 | B2 * | 10/2012 | Case .............................. 623/1.11 |
| 8,348,997 | B2 | 1/2013 | Thompson et al. |
| 8,388,599 | B2 * | 3/2013 | Warnack ....................... 604/509 |
| 2005/0038509 | A1 | 2/2005 | Ashe |
| 2005/0137701 | A1 * | 6/2005 | Salahieh et al. .............. 623/2.38 |
| 2005/0228495 | A1 | 10/2005 | Macoviak |
| 2006/0271081 | A1 | 11/2006 | Realyvasquez |
| 2008/0275550 | A1 | 11/2008 | Kheradvar et al. |

OTHER PUBLICATIONS

USPTO Final Office Action with notification date of Jan. 31, 2014, in related U.S. Appl. No. 12/899,231.

* cited by examiner

*Primary Examiner* — Bruce E Snow
*Assistant Examiner* — Brian Dukert
(74) *Attorney, Agent, or Firm* — Brian R. Pollack; Day Pitney LLP

(57) ABSTRACT

The present embodiments relate to systems and methods for treating lumenal valves. Particularly, and in accordance with one aspect, the present disclosure is directed to methods and systems for partial or complete replacement of lumenal valves. An exemplary catheter in accordance with the disclosure includes an elongate body having a proximal end and a distal end, and a retractable sheath mounted on the elongate body proximate the distal end. The sheath and elongate body cooperating to define a first annularly-shaped compartment between the body and sheath. The catheter further includes a valve prosthesis mounted in the compartment, the prosthesis having proximal and distal ends connected to a means for deploying the valve prosthesis from the catheter.

21 Claims, 9 Drawing Sheets

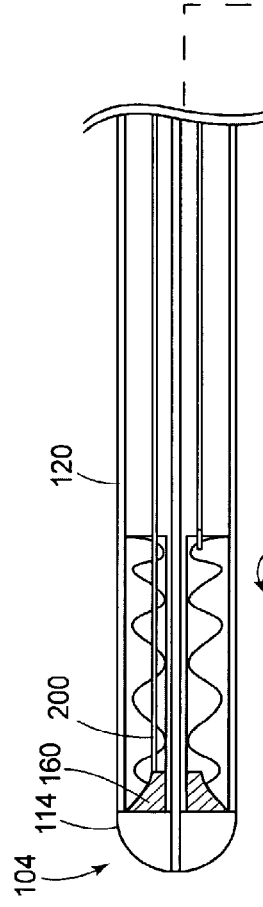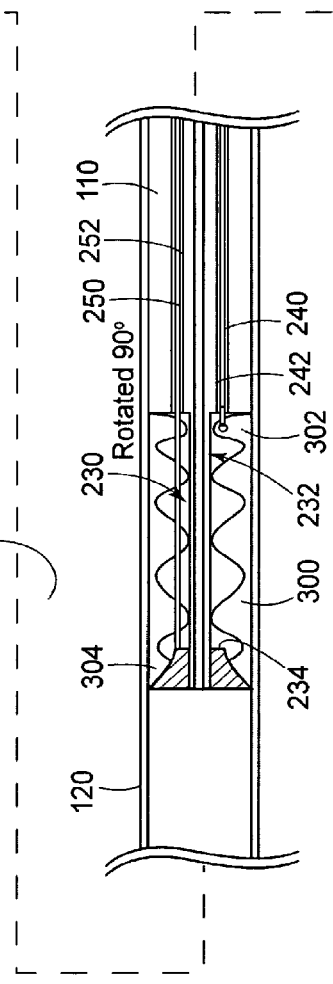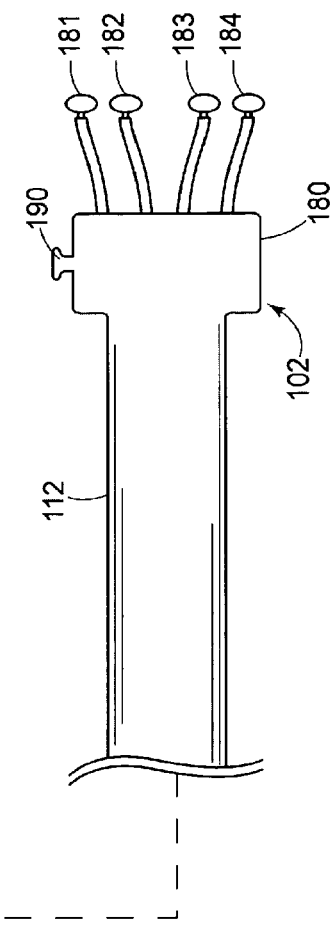

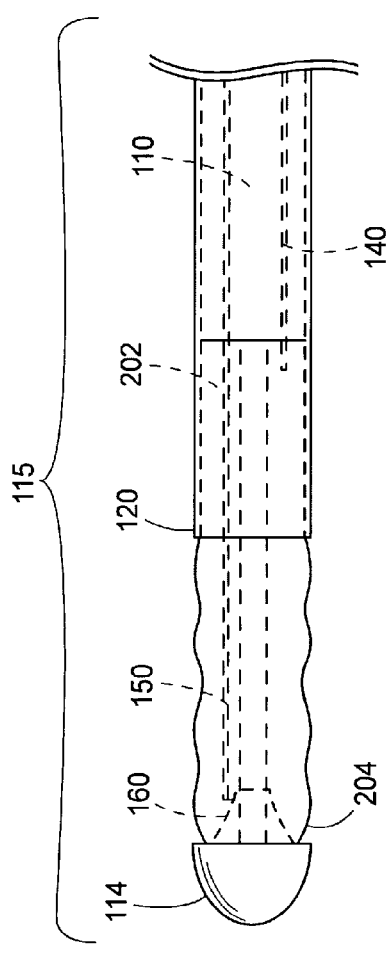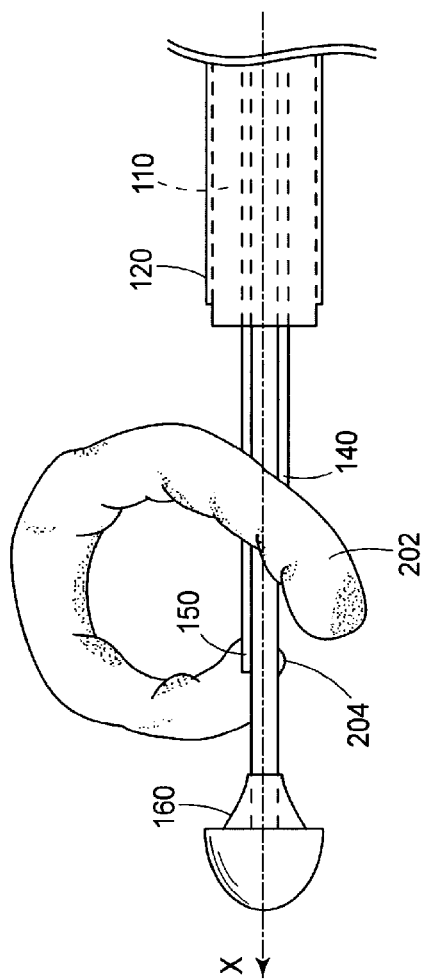
Fig. 4(A)
Fig. 4(B)

SYSTEMS AND METHODS FOR TREATING LUMENAL VALVES

CROSS-REFERENCE TO RELATED APPLICATION

This patent application is a division of and claims the benefit of priority to U.S. patent application Ser. No. 12/899,231, filed Oct. 6, 2010, which in turn claims the benefit of priority to U.S. Provisional Patent Application No. 61/249,020, filed on Oct. 6, 2009. Each of the aforementioned patent applications is incorporated by reference herein in its entirety.

BACKGROUND OF THE INVENTION

1. Field of the Invention

The present embodiments relate to systems and methods for treating lumenal valves. Particularly, and in accordance with one aspect, the present disclosure is directed to methods and systems for partial or complete replacement of lumenal valves.

2. Description of Related Art

Recently, there has been increasing consideration given to the possibility of using, as an alternative to traditional cardiac-valve prostheses, valves designed to be implanted using minimally-invasive surgical techniques or endovascular delivery (so-called "percutaneous valves"). Implantation of a percutaneous valve is a far less invasive act than the surgical operation required for implanting traditional cardiac-valve prostheses.

These expandable prosthetic valves typically include an anchoring structure or armature, which is able to support and fix the valve prosthesis in the implantation position, and prosthetic valve elements, generally in the form of leaflets or flaps, which are stably connected to the anchoring structure and are able to regulate blood flow.

An advantage of these expandable prosthetic valves is that they enable implantation using various minimally invasive or sutureless techniques. One application for such an expandable valve prosthesis is for aortic valve replacement. Various techniques are generally known for implanting such an aortic valve prosthesis and include percutaneous implantation (e.g., transvascular delivery through a catheter), dissection of the ascending aorta using minimally invasive thoracic access (e.g., mini-thoracotomy), and transapical delivery wherein the aortic valve annulus is accessed directly through an opening near the apex of the left ventricle. Note that the percutaneous and thoracic access approaches involve delivering the prosthesis in a direction opposing blood flow (i.e., retrograde), whereas the transapical approach involves delivering the prosthesis in the same direction as blood flow (i.e., antegrade). Similar techniques may also be applied to implant such a cardiac valve prosthesis at other locations (e.g., a pulmonary valve annulus).

However, to date, such systems have involved delivery of large implantable devices on catheters having very large profiles, necessitating unfavorable methods of delivery. There is thus a continued need in the art for devices and associated approaches for delivering replacement valves percutaneously with minimal adverse effects on the patient. The presently disclosed embodiments provide solutions for these needs.

SUMMARY OF THE INVENTION

Advantages of the present invention will be set forth in and become apparent from the description that follows. Additional advantages of the invention will be realized and attained by the methods and systems particularly pointed out in the written description and claims hereof, as well as from the appended drawings.

To achieve these and other advantages and in accordance with the purpose of the invention, as embodied herein, in one aspect, the invention includes a catheter. The catheter includes an elongate body having a proximal end and a distal end, and a retractable sheath mounted on the elongate body proximate the distal end. The sheath and elongate body cooperate to define a first annularly-shaped compartment between the body and sheath. The catheter can further include a means, such as a first linkage, extending from a proximal region of the compartment toward the proximal end of the catheter to help deploy a valve prosthesis. The catheter can further include means, such as a second linkage, extending from a distal region of the compartment toward the proximal end of the catheter to help deploy a valve prosthesis. The catheter further includes a valve prosthesis mounted in the compartment, the prosthesis having a proximal end attached to the first linkage and a distal end attached to the second linkage.

In further accordance with the disclosed embodiments, the catheter may further include a guide for directing the path of travel of the first linkage and second linkage to facilitate deployment of the valve prosthesis. The sheath is preferably adapted and configured to be retracted along a longitudinal axis of the catheter to expose the valve prosthesis. The first linkage and second linkage are preferably adapted and configured to deploy the valve prosthesis when the sheath is in a retracted position by advancing the second linkage in a proximal direction and by advancing the first linkage in a distal direction.

In accordance with a further aspect, the valve prosthesis is preferably in a generally longitudinal orientation prior to deployment, and is reoriented into a second, generally arcuate orientation when the second linkage is advanced in a proximal direction and when the first linkage is advanced in a distal direction.

In accordance with still a further aspect, the sheath and elongate body may cooperate to define a second annularly-shaped compartment therebetween, the second annularly-shaped compartment being displaced along a longitudinal axis of the catheter from the first compartment. In accordance with this embodiment, the catheter may further include a third linkage extending from a proximal region of the second compartment toward the proximal end of the catheter, a fourth linkage extending from a distal region of the second compartment toward the proximal end of the catheter, and a second valve prosthesis mounted in the second compartment, wherein the second prosthesis has a proximal end attached to the third linkage and a distal end attached to the fourth linkage.

In further accordance with the disclosed embodiments, the catheter may further include a second guide for directing the path of travel of the third linkage and fourth linkage to facilitate deployment of the second valve prosthesis. The sheath may be adapted and configured to be retracted along the longitudinal axis of the catheter to expose the second valve prosthesis. The third linkage and fourth linkage are preferably adapted and configured to deploy the second valve prosthesis when the sheath is in a retracted position by advancing the fourth linkage in a proximal direction and by advancing the third linkage in a distal direction. The second valve prosthesis is preferably in a generally longitudinal orientation prior to deployment, and is reoriented into a second, generally arcuate orientation when the fourth linkage is advanced in a proximal direction and when the third linkage is advanced in a distal direction.

The disclosure further provides a deployable valve prosthesis for replacing at least a portion of a lumenal valve. The valve prosthesis includes a deformable body, wherein the deformable body may be arranged into a first generally longitudinal orientation suitable for mounting underneath the retractable sheath of a catheter. The deformable body may further be rearranged into a second orientation that is generally arcuate.

In further accordance with the disclosed embodiments, the deformable body may include shape memory material, such as a nickel-titanium alloy. In accordance with another aspect, the deformable body may be constructed at least in part of a scaffolding material. The deformable body may have a generally serpentine shape. In accordance with a further aspect, the valve prosthesis can further include at least one deployable valve leaflet attached to the deformable body, wherein the valve leaflet is fully deployed upon implantation of the valve prosthesis.

The present disclosure also provides a method for delivering a valve prosthesis. the method includes advancing a distal portion of a catheter to a target location proximate a valve within a patient's lumenal system, withdrawing a sheath on the catheter to expose a valve prosthesis, the valve being in a generally longitudinal orientation prior to withdrawing the sheath, and deforming the valve prosthesis from the generally longitudinal orientation into a second, generally arcuate orientation.

In accordance with a further aspect of the disclosed embodiments, the valve prosthesis may be deformed from the generally longitudinal orientation into the generally arcuate orientation by drawing a first end of the valve prosthesis toward a second end of the valve prosthesis. The valve prosthesis may lie in a plane that is generally parallel to the longitudinal axis of the catheter when the first end of the valve prosthesis is drawn toward a second end of the valve prosthesis. The method can further include the step of rotating the valve prosthesis out of the plane generally parallel to the longitudinal axis of the catheter into a plane that is generally perpendicular to the longitudinal axis of the catheter.

In accordance with a further aspect, the method may further include spreading the valve prosthesis and aligning it with a portion of the annulus of the valve of a patient. In accordance with one embodiment, the existing valve leaflet of the patient may be pushed against the valve annulus or vessel wall when the valve prosthesis is aligned. The method may further include attaching the valve prosthesis to the valve annulus of the patient. In accordance with one embodiment, the installed valve prosthesis may occupy about half of the circumference of the valve annulus when installed.

In accordance with still a further aspect, the method may further include installing a second valve prosthesis adjacent the first valve prosthesis, wherein the second valve prosthesis substantially occupies the portion of the circumference of the valve annulus not occupied by the previously installed valve prosthesis.

In accordance with still another embodiment, the first and second valve prostheses may be installed proximate different valves of a patient within a given lumen. If desired, the first valve prosthesis may have a different size compared to the second valve prosthesis, such as if the different valves of the patent are of different sizes.

It is to be understood that the foregoing general description and the following detailed description are exemplary and are intended to provide further explanation of the invention claimed.

The accompanying drawings, which are incorporated in and constitute part of this specification, are included to illustrate and provide a further understanding of the method and system of the invention. Together with the description, the drawings serve to explain principles of the invention.

BRIEF DESCRIPTION OF THE DRAWINGS

FIG. 2A is a cross-sectional view of a second exemplary embodiment of a catheter made in accordance with the present disclosure.

FIG. 2B is a cross-sectional view of the retractable sheath of the second exemplary embodiment of the catheter made in accordance with the present disclosure.

FIG. 2C is a cross-sectional view of the manifold of the second exemplary embodiment of the catheter made in accordance with the present disclosure.

FIG. 4(A) depicts a first aspect of an exemplary method of delivering a prosthesis in accordance with the present disclosure.

FIG. 4(B) depicts a second aspect of an exemplary method of delivering a prosthesis in accordance with the present disclosure.

DETAILED DESCRIPTION OF PREFERRED EMBODIMENTS

Reference will now be made in detail to the present preferred embodiments of the invention, examples of which are illustrated in the accompanying drawings. The method and corresponding steps of the invention will be described in conjunction with the detailed description of the system.

As mentioned above, there is a continuing need for improved valve prostheses and associated devices and methods for delivery. As an illustrative non-limiting example, devices and associated methods described herein may be used to treat, among other things, vascular valve dysfunction and/or insufficiency in patients with Congestive Heart Failure (CHF) and or venous leg edema with symptoms that may include, for example, mitral regurgitation and venous insufficiency. In such cases, valve dysfunction occurs because of dilation, or enlargement, of the heart and/or veins and causes dysfunction of the valves. Venous insufficiency leads to edema of the legs while mitral regurgitation leads to decreased ventricular function. These conditions necessitate a need for less invasive procedures. Percutaneous procedures enable a non surgical approach to treat symptoms via a partial or complete valve replacement in a stepwise fashion. Current percutaneous procedures and or devices are limited in their ability to treat the full potential patient populations. Notably, it is observed herein that a partial and/or complete replacement may provide potential benefit over surgical and percutaneous methods for repair or complete replacement.

Current procedure requires one to two access points from the femoral. In accordance with the disclosed embodiments, it is possible to use percutaneous approaches to partially or completely replace heart valves or venous valves with a valve prosthesis by way of a transceptal or from a femoral retrograde approach. Using such approaches it becomes possible, for example, to achieve a partial or complete replacement of the mitral valve in a stepwise fashion using percutaneous methods.

The approaches herein may be used, for example, for treatment of patients with class I and Class 2 CHF. These classes of patients currently are not good surgical candidates. Opportunities thus exist to treat these patients percutaneously and in conjunction with other percutaneous procedures. Patients with venous edema represent a significantly larger patient population than CHF. Current methods to treat edema include pressure bandages in order to elevate symptoms. It is believed that the disclosed embodiments provide a novel approach that can correct valve dysfunction.

Thus, in accordance with one aspect of the disclosed embodiments, a catheter is provided including an elongate body, a retractable sheath, and including a deployable valve prosthesis.

Figure 1:
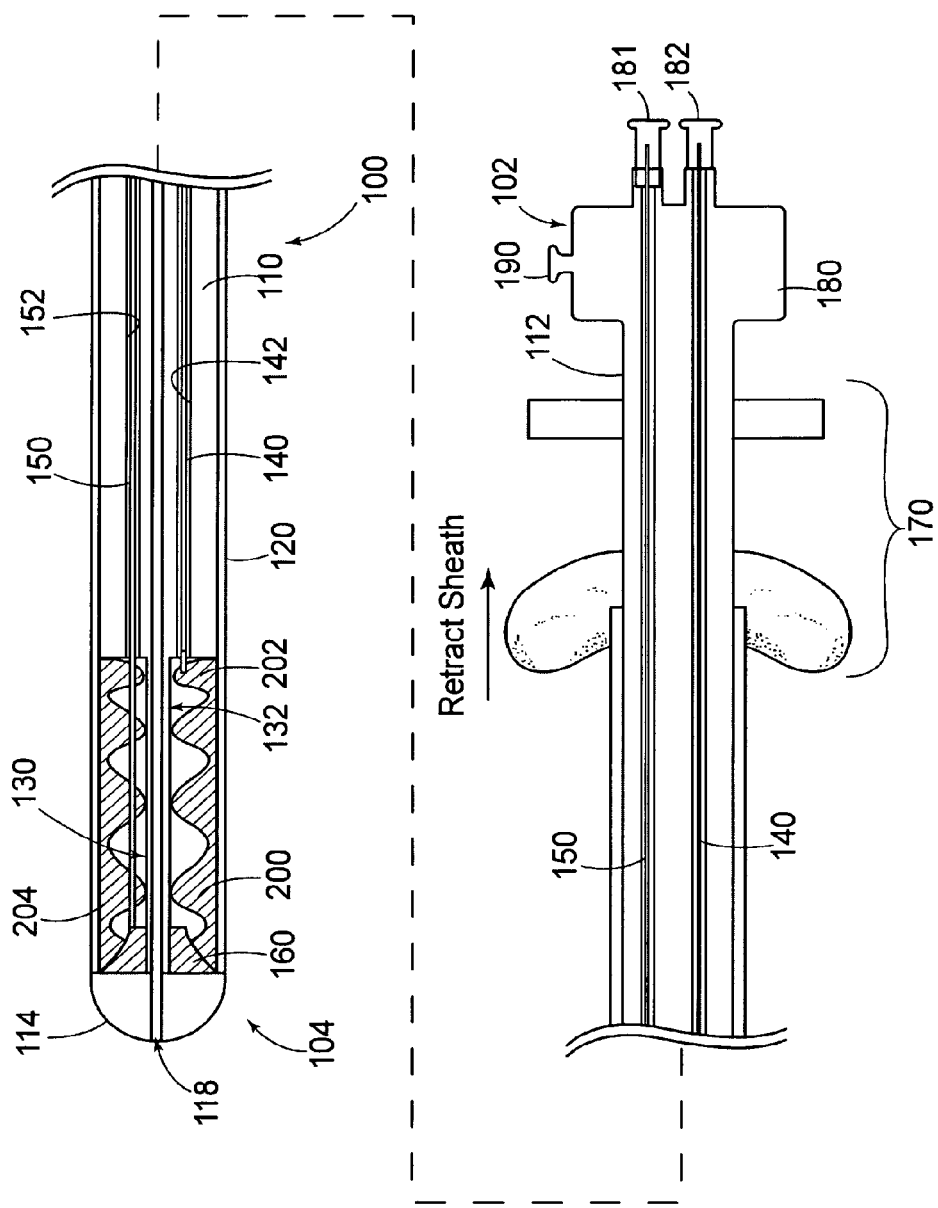
FIG. 1 is a cross-sectional view of a first exemplary embodiment of a catheter made in accordance with the present disclosure.

For purpose of explanation and illustration, and not limitation, a partial view of an exemplary embodiment of a catheter in accordance with the present disclosure is shown in FIG. 1 and is designated generally by reference character 100. Other aspects of catheters and associated methods in accordance with the present disclosure, or aspects thereof, are provided in FIGS. 2-12, as will be described.

As depicted in FIG. 1, catheter 100 includes an elongate body 110 having a proximal end 112, a distal end 114, and a retractable sheath 120 mounted on the elongate body 110 proximate the distal end 114. The sheath 120 and elongate body 120 cooperate to define a first annularly-shaped compartment 130 between the body and sheath for receiving a valve prosthesis 200, described in detail below.

As further depicted in FIG. 1, the catheter 100 includes means to facilitate deploying the valve prosthesis 200. For purposes of illustration and not limitation, as illustrated herein, such means in part includes a first linkage 140. First linkage 140 extends from a proximal region 132 of the compartment 130 toward the proximal end 102 of the catheter 100 to help deploy valve prosthesis 200. As depicted in FIG. 1, catheter 100 further includes a second linkage 150 extending from a distal region 134 of the compartment 130 toward the proximal end 102 of the catheter 100 to help deploy the valve prosthesis 200.

As depicted in FIG. 1, catheter 100 further includes a valve prosthesis 200 mounted in the compartment 130, the prosthesis having a proximal end 202 attached to the first linkage 140 and a distal end 204 attached to the second linkage 150. Prosthesis 200, as illustrated, is presented as a valve prosthesis. Other embodiments of prostheses are described below. In an undeployed state, prosthesis 200 is in a generally longitudinal configuration. However, during and after deployment, as illustrated in FIGS. 4(B)-7, prosthesis 200 has a generally annular configuration. As depicted in FIG. 7, upon deployment, prosthesis includes a peripheral region 206 including reinforcing structural material 212 such as scaffolding, and a leaflet 208 having an edge 209 made, for example, from a polymeric membrane 216. The structural material may include metallic and/or polymeric materials. Preferably, structural material 212 includes shape memory material, such as various alloys of nickel and titanium. It will be recognized that a variety of structures can be used for structural material 212 without departing from the spirit or scope of the disclosed embodiments. Concerning membrane 216, a variety of biocompatible materials can be used, such as ePTFE described, for example, in U.S. Pat. No. 6,436,135, which is incorporated by reference herein it its entirety. A variety of other polymeric, composite or biological materials may be used. For example, if desired, cellular content may be used and/or structural components from cadavers may be used as long as the materials are suitable for implantation.

As further depicted in FIG. 1, catheter 100 may further include a guide 160 for directing the path of travel of the first linkage 140 and second linkage 150 to facilitate deployment of the valve prosthesis 200. As depicted, guide 160 is generally bell-shaped, and acts to cause linkages 140, 150 to splay apart during deployment of prosthesis 200 to help prosthesis 200 to take on an arcuate shape. Particularly, a pull wire 162 or similar structure can be provided to advance guide 160 proximally to facilitate deployment. However, it will be recognized that guide 160 need not be provided. Instead, if shape memory material is used to make prosthesis 200 and/or linkages 140, 150, deployment may be facilitated by such components changing shape by retracting sheath 120 proximally and by manipulating linkages 140, 150 along a proximal/distal direction, as well as rotationally.

Figure 3:
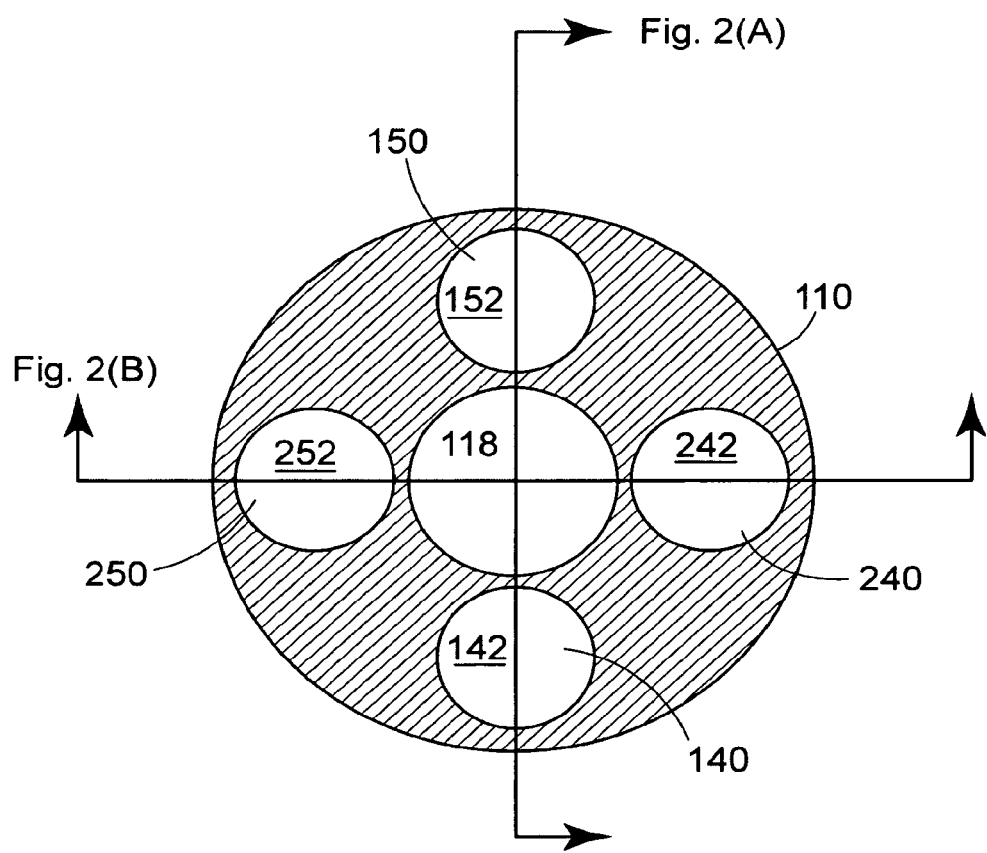
FIG. 3 is a cross sectional view of a portion of the exemplary embodiment of FIG. 2A-2C.

Linkages 140, 150 (and 240, 250, described below) may be made from a variety of materials, such as hypotubes made from stainless steel (and having a very small profile), or may be solid metallic or composite members, such as carbon fiber reinforced materials. As depicted in FIG. 3, inner member 110 may include a variety of lumens along its length, such as for advancing or retracting linkages 140, 150 (and 240, 250), as well as for pull wire 162, or for a guidewire. Specifically, a guidewire lumen 118 is provided, if desired. It will also be recognized that catheter 100 can be delivered in a guiding catheter, and need not be provided with its own guidewire lumen 118.

Referring again to FIG. 1, sheath 120 is preferably adapted and configured to be retracted along a longitudinal axis of the catheter to expose the valve prosthesis using an actuator 170, described in more detail below. The first linkage 140 and second linkage 150 are preferably adapted and configured to deploy the valve prosthesis 200 when the sheath 120 is in a retracted position by advancing the second linkage 150 in a proximal direction and by advancing the first linkage 140 in a distal direction. The method of deployment of valve prosthesis 200 using catheter 100 is described in detail below.

In accordance another embodiment, as depicted in FIG. 2B, if desired, it is possible to provide a second deployable valve prosthesis 300. The means for retaining, releasing and delivering the second prosthesis may be very similar to the first prosthesis 200. The same sheath 120 may be used to house the second prosthesis 300 in cooperation with the elongate body 110 to define a second compartment 260 to store the prosthesis until it is deployed. In accordance with this embodiment, the catheter may further include a third linkage 240 extending from a proximal region of the second compartment 230 toward the proximal end 102 of the catheter and a fourth linkage 250 extending from a distal region of the second compartment 230 toward the proximal end of the catheter. As depicted, the second prosthesis 300 has a proximal end 302 attached to the third linkage 240 and a distal end 304 attached to the fourth linkage 250.

Concerning the relative positioning of multiple prostheses on catheter 100, prostheses 200, 300 may be disposed in opposite orientations from one another rotationally. As depicted, for sake of convenience, prostheses are disposed on catheter 100 at a relative rotation of 90 degrees to permit linkages 140, 150, 240, 250 to each occupy a lumen (142, 152, 242, 252) in a different quadrant of the cross section of elongate body 110 as depicted in FIG. 3.

Elongate body 110 may be made in a variety of ways and from a variety of materials. For example, elongate body 110 may be made from a variety of materials, including metal, plastic and composite materials. Metal tubes such as stainless steel hypotubes can be used for one or more portions of elongate body 110 for enhanced pushability alone or in combination with other suitable materials. For example, FIG. 3 discloses a cross section of the elongate body 110 of the exemplary catheter illustrated in FIGS. 1-2A and 2B, including a plurality of lumens that may be used for directing linkages to the distal region of the catheter. If metal tubular components are used to make elongate body 110, they are preferably coated with a lubricious material such as PTFE, other hydrophobic materials or hydrophilic materials. Multi-layered polymeric tubes can also be used to form elongate member 110 that can be formed by coextrusion, dipping processes, or by shrinking tubing layers over one another over a mandrel. Moreover, polymeric tubular members can also be formed by charging a mandrel with static electricity, applying plastic in powder or granular form to the mandrel to form a layer of plastic over the mandrel, and by heating the mandrel to cause the particles to fuse. Multilayered polymeric tubes can also be used that include metallic or nonmetallic braiding within or between layers of the tube. A carbon tube can also be used, as well as fiber-reinforced resin materials. In accordance with another embodiment, elongate body 110 may be provided with a decreasing stiffness along its length from proximal end 112 to distal end 114. As will be further appreciated by those of skill in the art, elongate body 110 may include a multiple-lumen extrusion including two, three, four, or more lumens along part of or substantially the entire length of elongate body 110 as depicted in FIG. 3. Moreover, stiffening wires can be used at various locations along elongate body to provide stiffness transitions between relatively stiffer regions and less stiff regions, as well as proximate regions of stress concentration, such as guidewire exit ports and the like. In accordance with one embodiment, a guidewire lumen 118 is provided along substantially the entire length of elongate body 110 as with typical over the wire ("OTW") catheters. In accordance with another embodiment, a guidewire lumen 118 is provided only proximate the distal region of elongate body 110 to permit use of catheter 100 as a rapid exchange ("RX") catheter.

Sheath 120 may be made from a variety of materials. Preferably, sheath 120 includes a multi-layered co-extrusion, such as those described in U.S. Pat. No. 6,464,683 to Samuelson or U.S. Pat. No. 5,538,510 to Fontirroche. Each of the aforementioned patents is incorporated by reference herein in its entirety.

As further depicted in FIG. 1, an actuator 170 is provided for selectively retracting sheath 120. Actuator 170 can take on a variety of forms, such as those depicted in U.S. Pat. No. 6,488,694 to Lau and U.S. Pat. No. 5,906,619 to Olson, the specifications of which are incorporated herein by reference. In addition, as depicted in FIGS. 1 and 2C, a manifold 180 is provided including a plurality of actuators 181-184 for controlling linkages 140, 150, 240, 250. However, as will be appreciated, manifold may also include flush ports 190 for preparing or cleaning catheter 100.

Any surface of various components of the catheters described herein or portions thereof can be provided with one or more suitable lubricious coatings to facilitate procedures by reduction of frictional forces. Such coatings can include, for example, hydrophobic materials such as Polytetrafluoroethylene ("PTFE") or silicone oil, or hydrophilic coatings such as Polyvinyl Pyrrolidone ("PVP"). Other coatings are also possible, including, echogenic materials, radiopaque materials and hydrogels, for example.

The present disclosure also provides methods for delivering a valve prosthesis. In accordance with one illustrative embodiment, reference is made to the embodiment of FIG. 1. First, with reference to FIG. 4(A), the method includes advancing a distal portion 115 of a catheter 100 to a target location proximate a valve within a patient's lumenal system. The method further includes withdrawing a sheath 120 on the catheter 100 to expose a valve prosthesis 200, the valve prosthesis 200 being in a generally longitudinal orientation prior to withdrawing the sheath 120. Next, as illustrated in FIG. 4(B), the valve prosthesis is deformed from a pre-deployment, generally longitudinal orientation, into a second, generally arcuate orientation. In the embodiment of FIG. 4(B), this is accomplished by advancing linkage 140 distally, and advancing linkage 150 proximally. As can be seen this results in the first end 202 of the valve prosthesis 200 being drawn toward second end 204 of the valve prosthesis 200. As depicted in FIG. 4(B), the valve prosthesis 200 may lie in a plane that is generally parallel to the longitudinal axis X of the catheter when the first end 202 of the valve prosthesis 200 is drawn toward the second end 204 of the valve prosthesis 200.

Figure 5:
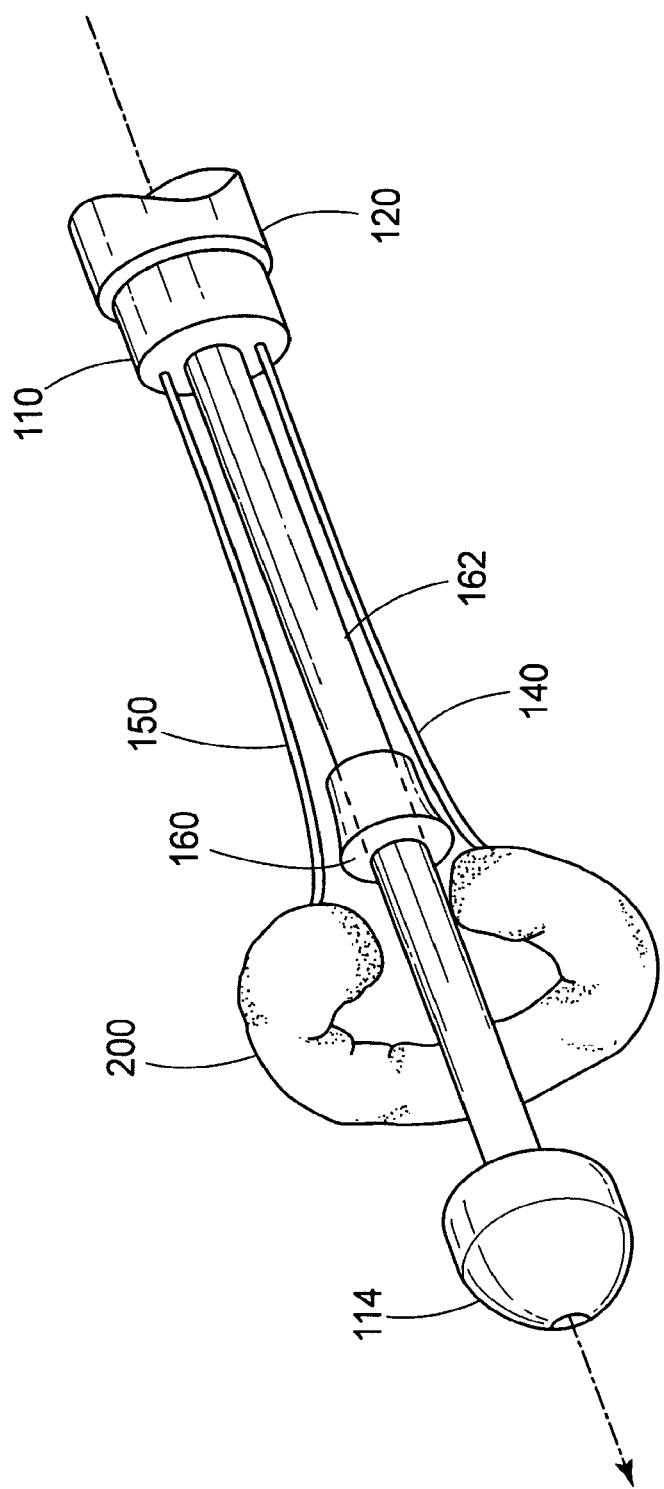
FIG. 5 depicts a third aspect of an exemplary method of delivering a prosthesis in accordance with the present disclosure.

As illustrated in FIG. 5, the method can further include the step of rotating the valve prosthesis 200 out of the plane generally parallel to the longitudinal axis of the catheter into a plane that is generally perpendicular to the longitudinal axis of the catheter. As illustrated in FIG. 5, at this point, linkages 140, 150 are about the same distance from the proximal end of the catheter, but guide member 160 has not yet been fully actuated to continue deployment.

Figure 6:
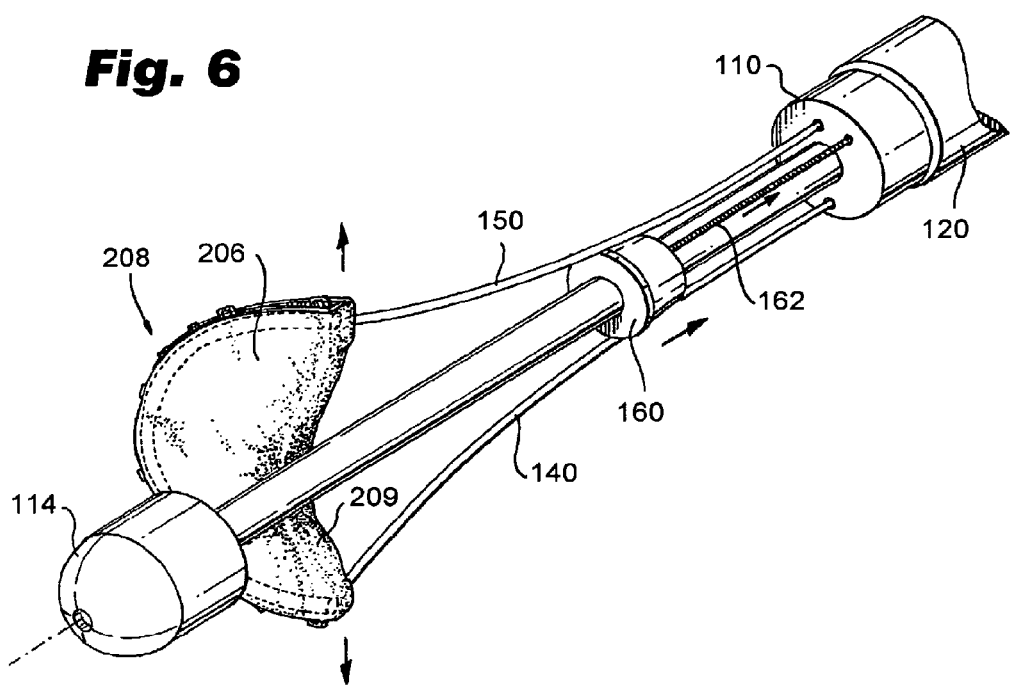
FIG. 6 depicts a fourth aspect of an exemplary method of delivering a prosthesis in accordance with the present disclosure.
Figure 7:
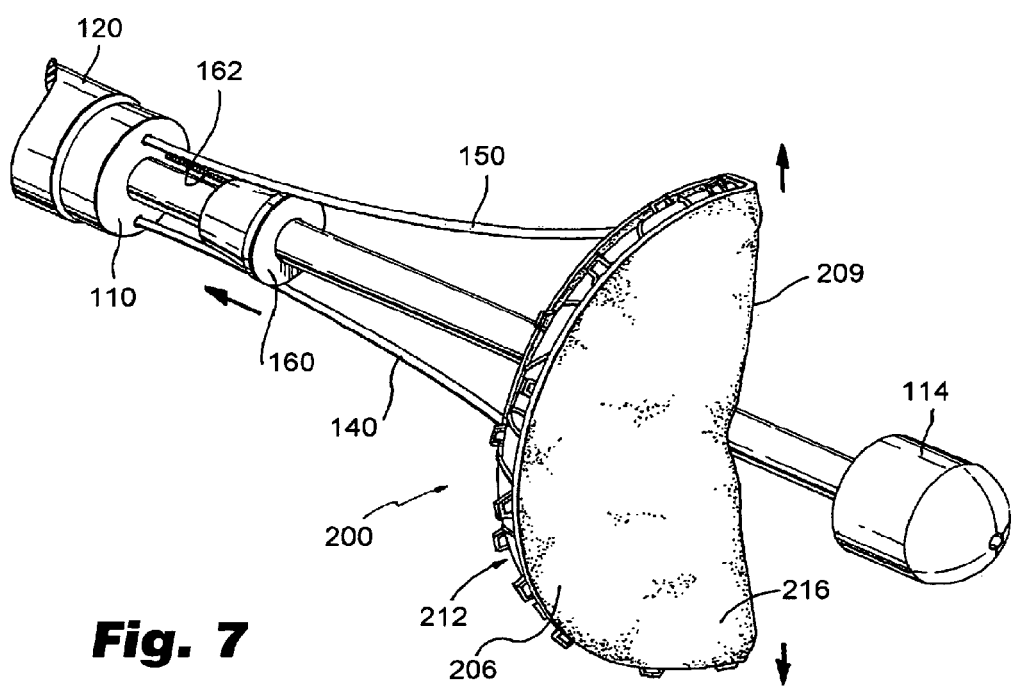
FIG. 7 depicts an exemplary valve prosthesis made in accordance with the present disclosure in a deployed condition.

As depicted in FIG. 6, the method may further include deploying a guide member (e.g., 160 by pulling pull wire 162), to cause linkages 140, 150 to splay outwardly to cause prosthesis 200 to fully deploy into a condition illustrated in FIG. 7. At this point, prosthesis 200 can be positioned within a patient's valve annulus and secured by various retainers, such as sutures and clips. In accordance with one embodiment, prosthesis may simply be installed over the patient's existing valve leaflet, causing the pre-existing leaflet to be pinned to the side of the vessel wall. Once properly installed, edge 209 of leaflet 208 will substantially align with the adjoining pre-existing leaflet. However, if desired, a second prosthesis 300 may be installed proximate the first prosthesis to accomplish a full replacement. The second prosthesis 300 may be provided by using a catheter made in accordance with the teachings relating to FIG. 2A-2C herein, or simply by using a second catheter made in accordance with the teachings relating to FIG. 1.

As will be appreciated by those of skill in the art, a variety of procedures may be accomplished using the teachings herein. For example, a catheter made in accordance with the teachings relating to FIG. 2A-2C herein to perform partial valve replacements at adjacent valves in a patient's vein, such as for treating leg edema. Accordingly, the valve prostheses can be provided in different sizes to allow for the reduction in size in sequential venous valves to permit one catheter to be used to make two valve replacements.

Figure 8:
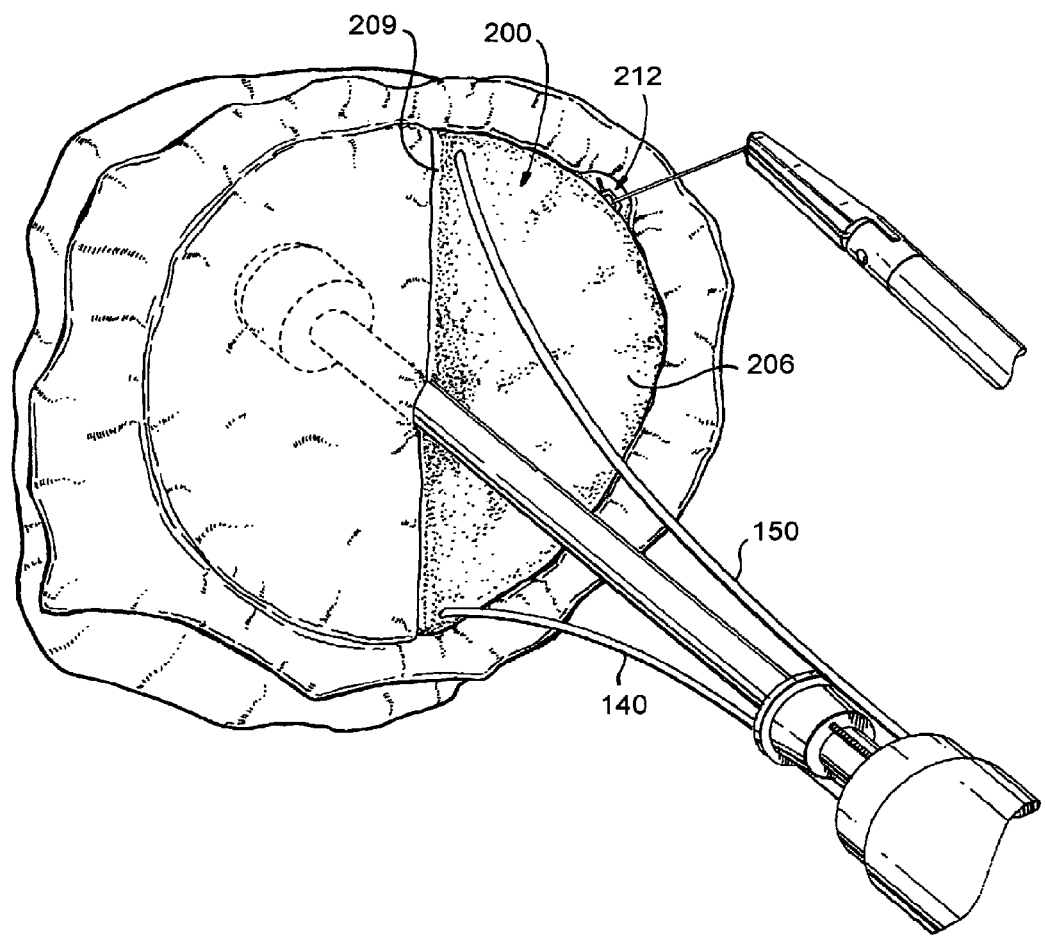
FIG. 8 depicts a view of an exemplary prosthesis installed in a valve of an animal heart resulting in a partial valve replacement.
Figure 9:
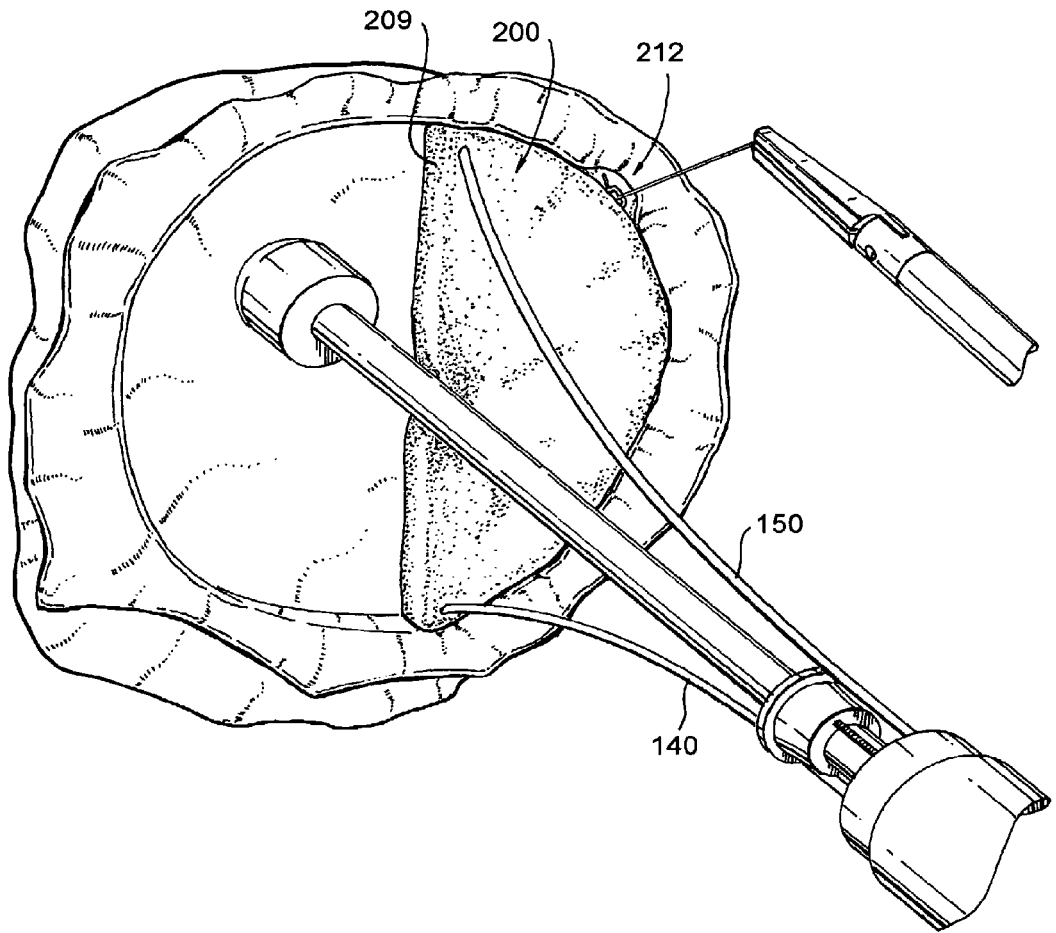
FIG. 9 depicts a view of an exemplary prosthesis installed in the valve of an animal heart in a first portion of a complete valve replacement procedure.
Figure 10:
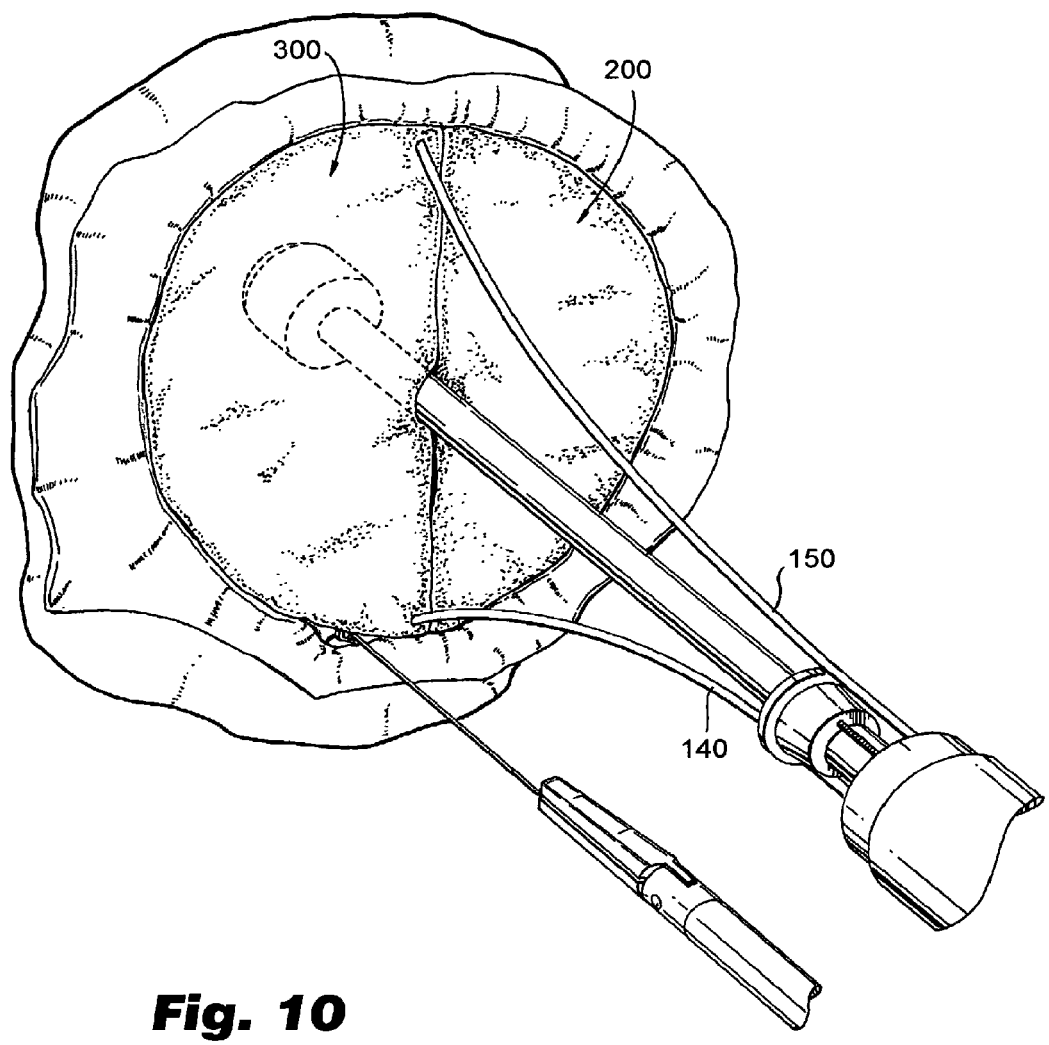
FIG. 10 depicts two exemplary prostheses installed as a part of a complete valve replacement in an animal heart.

FIGS. 8-10 illustrate partial and complete valve replacement using embodiments of prosthesis made and installed in accordance with the present disclosure. FIG. 8 depicts a view of an exemplary prosthesis installed in a cardiac valve, such as a mitral valve, of an animal heart. The procedure depicted in FIG. 8 is one where a single prosthesis 200 is installed, replacing only one of the valve leaflets. FIGS. 9-10 depicts a ventricular view of a similar procedure, but wherein both leaflets are replaced. In particular, FIG. 9 illustrates a single prosthesis installed, replacing one half of the valve, with the leaflet corresponding to the other half of the original valve being removed. FIG. 10 illustrates the addition of second valve prosthesis 300, resulting in a complete valve replacement, such as a mitral valve replacement. If desired, artificial valve chordae 273, 373 (such as sutures made of ePTFE or other suitable material) can be provided to connect the exposed edges 209, 309 of the leaflets to original chordae, or the papillary muscle where the original valve chordae were anchored.

As will be appreciated by those of skill in the art, the delivery catheters and associated methods described herein may be used to deliver a variety of devices within the lumenal system of a patent. In particular, such catheters and methods can be used whenever it is desired to deliver a device in a generally elongate form that is later oriented into a generally arcuate form. This approach permits delivery of relatively large devices, such as replacement valves for large lumens, on comparatively smaller profile catheters than used heretofore in the art. As such, it will be appreciated that such catheters and methods can be used to deliver such implants adapted (e.g., sized) for other applications, such as veins, arteries, the gastrointestinal tract, or any other body conduit/lumen that would benefit from such a valve apparatus.

The methods and systems of the present invention, as described above and shown in the drawings, provide for improved devices and methods for replacement of lumenal valves. It will be apparent to those skilled in the art that various modifications and variations can be made in the device and method of the present invention without departing from the spirit or scope of the invention. Thus, it is intended that the present invention include modifications and variations that are within the scope of the appended claims and their equivalents.

What is claimed is:

1. A catheter comprising:
   a) an elongate body having a proximal end and a distal end;
   b) a retractable sheath mounted on the elongate body proximate the distal end, the sheath and elongate body cooperating to define a first compartment therebetween for receiving a valve prosthesis;
   c) a first elongate generally rigid linkage extending from a proximal region of the compartment toward the proximal end of the catheter;
   d) a second elongate, generally rigid linkage extending from a distal region of the compartment toward the proximal end of the catheter; and
   e) a valve prosthesis for replacing a portion of a lumenal valve, the valve prosthesis including a leaflet attached to a deformable structural circumferential portion mounted in the compartment, the deformable structural circumferential portion of the valve prosthesis having a curved shape when fully deployed and having a first circumferential end and a second circumferential end separated by a gap that is spanned at least in part by the leaflet, the deformable structural circumferential portion having a proximal portion near the first circumferential end attached to the first linkage and a distal portion near the second circumferential end attached to the second linkage, wherein:
      i) the deployable valve prosthesis can be arranged into a first configuration wherein the deformable structural circumferential portion is generally straight and in an elongate orientation that is generally parallel to a longitudinal axis of the catheter when the valve prosthesis is disposed within the compartment between the elongate body and retractable sheath; and
      ii) the deployable valve prosthesis can be deployed from the first configuration into a second configuration wherein the deformable structural circumferential portion is curved and disposed in a plane generally perpendicular to the longitudinal axis of the catheter after the sheath is withdrawn.

2. The catheter of claim 1, further comprising a guide for directing the path of travel of the first linkage and second linkage to facilitate deployment of the valve prosthesis.

3. The catheter of claim 1, wherein the sheath is adapted and configured to be retracted along a longitudinal axis of the catheter to expose the valve prosthesis.

4. The catheter of claim 1, wherein the first linkage and second linkage are configured to deploy the valve prosthesis when the sheath is in a retracted position when the second linkage is moved in a proximal direction with respect to the elongate body and when the first linkage is moved in a distal direction with respect to the elongate body.

5. The catheter of claim 4, wherein the valve prosthesis is configured to be in a generally longitudinal orientation prior to deployment, and is configured to become reoriented into a second, generally arcuate orientation when the second linkage is moved in a proximal direction with respect to the elongate body and when the first linkage is moved in a distal direction with respect to the elongate body.

6. The catheter of claim 1, wherein the sheath and elongate body cooperate to define a second compartment therebetween, the second compartment being displaced along a longitudinal axis of the catheter from the first compartment.

7. The catheter of claim 6, wherein the catheter further comprises:
   a) a third linkage extending from a proximal region of the second compartment toward the proximal end of the catheter;
   b) a fourth linkage extending from a distal region of the second compartment toward the proximal end of the catheter; and
   c) a second valve prosthesis mounted in the second compartment, the second prosthesis having a proximal region attached to the third linkage and a distal region attached to the fourth linkage.

8. The catheter of claim 7, further comprising a second guide for directing the path of travel of the third linkage and fourth linkage to facilitate deployment of the second valve prosthesis.

9. The catheter of claim 7, wherein the sheath is adapted and configured to be retracted along the longitudinal axis of the catheter to expose the second valve prosthesis.

10. The catheter of claim 7, wherein the third linkage and fourth linkage are configured to deploy the second valve prosthesis when the sheath is in a retracted position when the fourth linkage is moved in a proximal direction with respect to the elongate body and when the third linkage is moved in a distal direction with respect to the elongate body.

11. The catheter of claim 10, wherein the second valve prosthesis is configured to be in a generally longitudinal orientation prior to deployment, and is configured to become reoriented into a second, generally arcuate orientation when the fourth linkage is moved in a proximal direction with respect to the elongate body and when the third linkage is moved in a distal direction with respect to the elongate body.

12. The catheter of claim 1, wherein the first and second linkages include a portion made from a hypotube.

13. The catheter of claim 1, wherein the first and second linkages are solid members.

14. The catheter of claim 13, wherein the first and second linkages include carbon fiber reinforced material.

15. The catheter of claim 1, wherein the first and second linkages include a nickel-titanium alloy.

16. The catheter of claim 1, wherein the elongate body is an inner member defining a plurality of lumens along its length.

17. The catheter of claim 16, wherein one of the lumens in the inner member includes a pull wire disposed therein.

18. The catheter of claim 16, wherein one of the lumens in the inner member includes a guide wire disposed therein.

19. The catheter of claim 1, wherein the deformable structural circumferential portion includes shape memory material.

20. The catheter of claim 1, wherein the second linkage is disposed alongside the prosthesis in the compartment before the sheath is withdrawn.

21. The catheter of claim 1, wherein the first and second linkages are splayed apart by expansion of the deployable valve prosthesis when the deployable valve prosthesis is in the second configuration, and wherein the first and second linkages can be manipulated to position the valve prosthesis while in the second configuration.

* * * * *